US012636495B2

(12) United States Patent
Francart et al.

(10) Patent No.: US 12,636,495 B2
(45) Date of Patent: May 26, 2026

(54) STIMULATION ARTEFACT MODIFICATION METHOD

(71) Applicant: KATHOLIEKE UNIVERSITEIT LEUVEN, Leuven (BE)

(72) Inventors: Tom Francart, Blanden (BE); Ben Somers, Leuven (BE)

(73) Assignee: KATHOLIEKE UNIVERSITEIT LEUVEN, Leuven (BE)

( * ) Notice: Subject to any disclaimer, the term of this patent is extended or adjusted under 35 U.S.C. 154(b) by 316 days.

(21) Appl. No.: 18/269,206

(22) PCT Filed: Dec. 22, 2021

(86) PCT No.: PCT/EP2021/087222
§ 371 (c)(1),
(2) Date: Jun. 22, 2023

(87) PCT Pub. No.: WO2022/136513
PCT Pub. Date: Jun. 30, 2022

(65) Prior Publication Data
US 2024/0131333 A1     Apr. 25, 2024
US 2024/0226554 A9     Jul. 11, 2024

(30) Foreign Application Priority Data
Dec. 24, 2020     (EP) ..................................... 20217311

(51) Int. Cl.
*A61N 1/36*          (2006.01)
(52) U.S. Cl.
CPC ............................... *A61N 1/36038* (2017.08)
(58) Field of Classification Search
CPC ............ A61N 1/36038; A61N 1/36039; A61N 1/0541; A61B 5/38; A61B 5/377
See application file for complete search history.

(56) References Cited

U.S. PATENT DOCUMENTS 9,044,155 B2     6/2015 Strahl
2006/0167369 A1     7/2006 Montgomery, Jr. et al.
(Continued)

FOREIGN PATENT DOCUMENTS

WO     2018170141 A1     9/2018
WO     2020124135 A1     6/2020

OTHER PUBLICATIONS

Extended European Search Report from corresponding European Patent Application No. EP20217311.8, Jun. 15, 2021.
(Continued)

*Primary Examiner* — Joseph M Dietrich
(74) *Attorney, Agent, or Firm* — Workman Nydegger

(57)          ABSTRACT

A computer-implemented method is provided for modifying a stimulation artefact in a measured electrical response of a subject to a stimulus. The method comprises: i) providing a first and a second signal. The first signal is a signal used as stimulus or a time-dependent signal derived from the stimulus and the second signal is a signal obtained as the measured electrical response to the stimulus; ii) determining a stimulus-response mapping between the first signal and the second signal; iii) identifying a feature of the determined stimulus-response mapping corresponding to the stimulation artefact; iv) determining a predicted electrical response corresponding to the identified feature of the determined stimulus-response mapping; and v) subtracting the predicted electrical response from the second signal to obtain a stimulation artefact modified measured electrical response.

14 Claims, 7 Drawing Sheets

(56)                     References Cited

U.S. PATENT DOCUMENTS

| | | |
|---|---|---|
| 2007/0118047 A1 | 5/2007 | Tracey et al. |
| 2015/0018699 A1 | 1/2015 | Zeng et al. |

OTHER PUBLICATIONS

International Search Report from corresponding PCT Application No. PCT/EP2021/087222, Mar. 11, 2022.

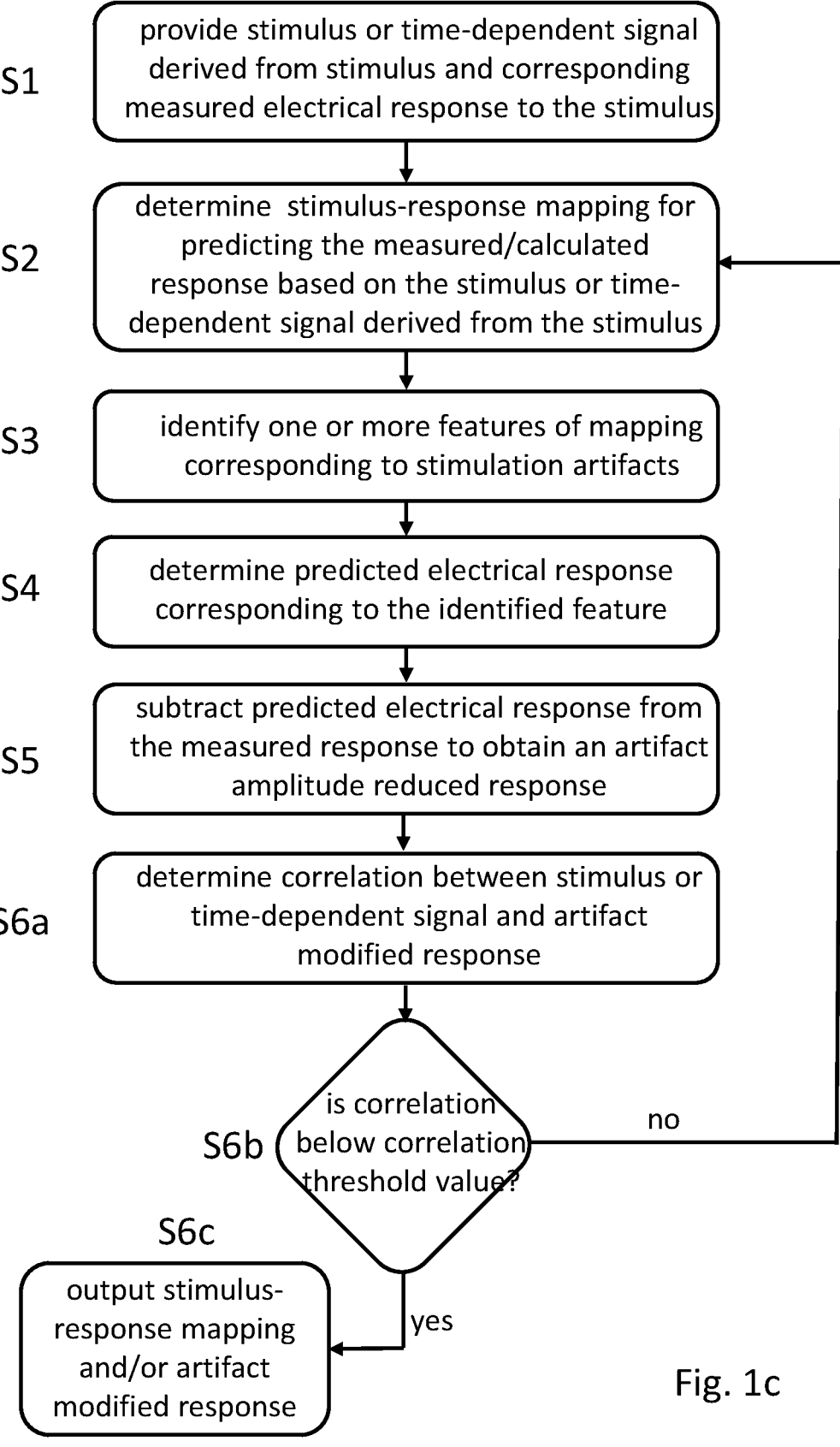

S1    provide stimulus or time-dependent signal derived from stimulus and corresponding measured electrical response to the stimulus S2    determine stimulus-response mapping for predicting the measured/calculated response based on the stimulus or time-dependent signal derived from the stimulus S3    identify one or more features of mapping corresponding to stimulation artifacts S4    determine predicted electrical response corresponding to the identified feature S5    subtract predicted electrical response from the measured response to obtain an artifact amplitude reduced response S6a   determine correlation between stimulus or time-dependent signal and artifact modified response S6b   is correlation below correlation threshold value?

no yes

S6c   output stimulus-response mapping and/or artifact modified response

Fig. 1c

Fig. 2(a)
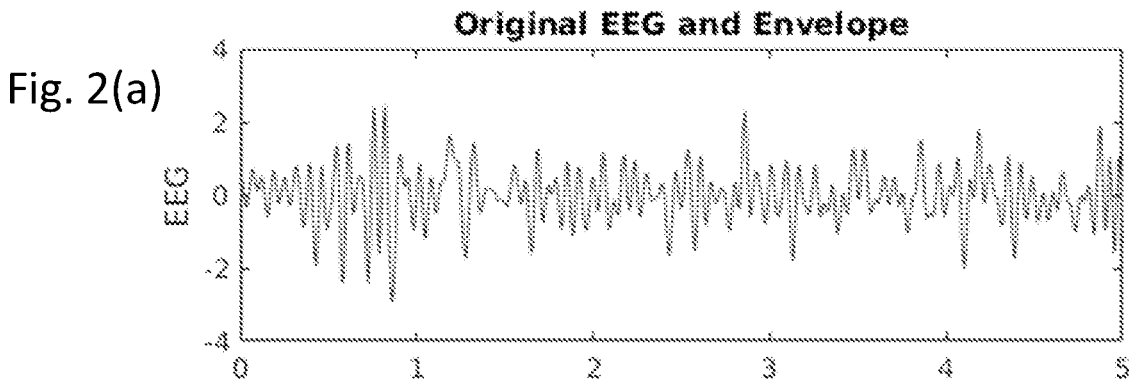
Fig. 2(b)
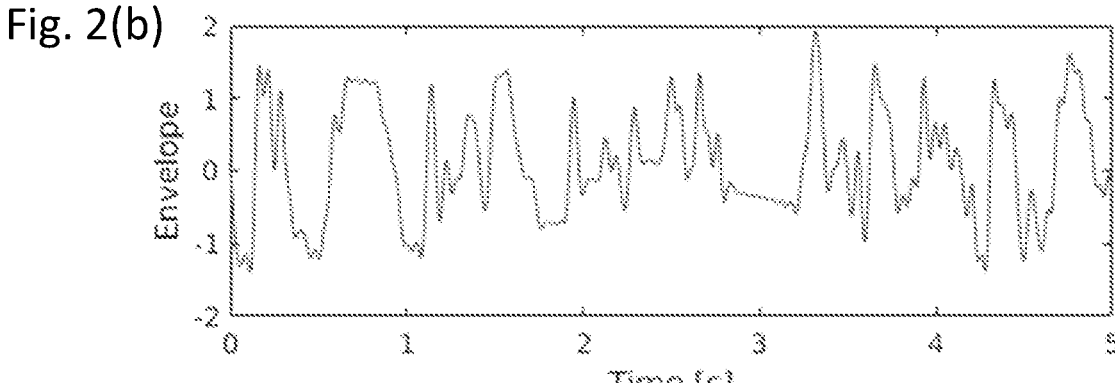
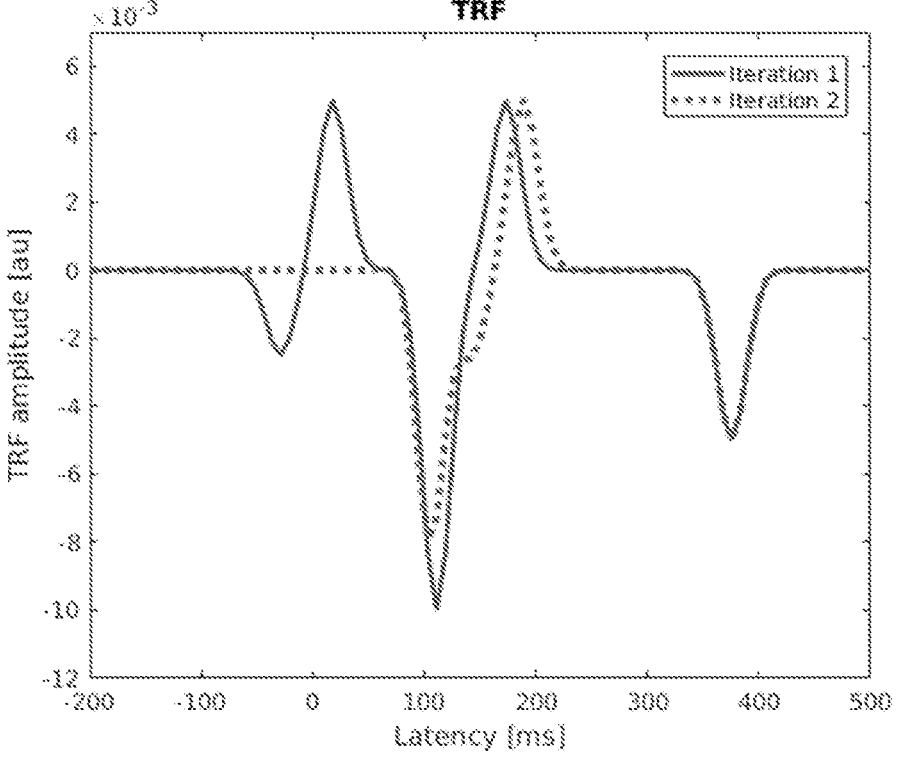
Fig. 3

STIMULATION ARTEFACT MODIFICATION METHOD

FIELD OF THE INVENTION

The present invention is generally related to the field of electrophysiological recording to a stimulus, and more particularly to methods for modifying a stimulation artefact in a measured electrical response of the subject to a stimulus.

BACKGROUND OF THE INVENTION

In a cochlear implant assessment procedure a subject wears a cochlear implant. An auditory stimulus is provided, for example by a loudspeaker. The cochlear implant receives the auditory stimulus and converts the audio signal to a series of electrical pulses that stimulate the auditory nerve of the subject, leading to a perception of sound in the brain of a subject, which may be a human or an animal.

A set of electroencephalography (EEG) probes are attached to the head of the subject for measuring the neural response of the subject. By comparing the neural response measured by the EEG probes with the auditory stimulus, the processing of the auditory stimulus by the brain of a subject can be assessed.

Due to the electrical nature of both the EEG measurement and the electrical stimulation provided by the cochlear implant to the auditory nerve of the subject, the measured EEG response may include both the desired neural response to the auditory signal and an unintentional recorded stimulus signal or waveform, generally referred to as stimulation artefacts or stimulus artefacts, which may be electrical, acoustical and/or mechanical in nature, without being limited thereto. For example, the stimulation artefacts may be caused by pickup by the EEG probes of electrical signals from the cochlear implant.

Stimulation artefacts, like, for example, electrical artefacts are in general much larger in amplitude than the neural response, which can impede the accurate measurement of the neural response.

Similarly, in a hearing test in which an auditory stimulus is provided to a subject by a stimulus-emitting electronic device, e.g. headphones, which is close to the subject's head, the measured EEG response can include additional unintentional recorded stimulus signals caused by, for example, transducer coils in the electronic device. Hence, reference may be made to electrical artefacts in the measured EEG response.

Removal of such stimulus artefacts using conventional signal processing methods based on signal decomposition is difficult as the electrical artefacts can temporally overlap, and be strongly correlated with the neural response. US2015/018699 A1 relates to closed-loop cochlear implant systems and methods for monitoring auditory evoked potentials from the peripheral and central auditory pathway to optimize speech processing. Paragraph of that application describes an artefact template subtraction technique which involves subtracting a template containing artefact only from a contaminated signal which contains both stimulation artefact and neural response. The template is generated by making assumptions about the shape of the stimulation artefact, for example assuming an exponential decay function. One limitation of this technique is that the assumed artefact function may not accurately describe the stimulation artefact. Another limitation is that this technique cannot be applied in cases of continuous stimulation by multiple pulses, in which stimulation artefacts can overlap with each other and a single template cannot be fitted. A further limitation is that a good fitting of the template to the signal may not be found easily and may lead to removal of one or more signal features that should not be removed.

Applications as described above would definitely benefit from a method, a computer program and a computer-readable medium comprising instructions to carry out the method of reliably and efficiently modifying, for example reducing the amplitude of, stimulation artefacts in a measured neural response which address at least some of the issues outlined above.

SUMMARY OF THE INVENTION

According to a first aspect of the present invention, there is provided a computer-implemented method of modifying a stimulation artefact in a measured electrical response of a subject to a stimulus. The method comprises:

i) providing a first and a second signal, said first signal being a signal used as stimulus or a time-dependent signal derived from the stimulus and the second signal being a signal obtained as the measured electrical response to the stimulus;

ii) determining a stimulus-response mapping between the first signal and the second signal;

iii) identifying a feature of the determined stimulus-response mapping corresponding to the stimulation artefact;

iv) determining a predicted electrical response corresponding to the identified feature of the determined stimulus-response mapping; and v) subtracting the predicted electrical response from the second signal to obtain a stimulation artefact modified measured electrical response.

It is an advantage of embodiments of the present invention that, by identifying a feature of the artefact in the stimulus-response mapping, the artefact can be modified, e.g. reduced in amplitude, in the response more efficiently and completely. The stimulus-response mapping, for example a temporal response function, is calculated without any prior knowledge or assumption of what the artefact should look like, like for example without the need of making use of a template making assumptions about the shape of the stimulation artefact.

It is an advantage of embodiments of the present invention that, by determining the stimulus-response mapping, features of the artefact can be more easily identified and thus separated from the signal corresponding to the obtained neural response. The stimulus-response mapping enables the latency difference between the artefact and the neural response to be exploited in order to easily identify and separate these features.

It is an advantage of embodiments of the present invention that the method can be automated without human input required for identifying the artefact features in the response.

It is an advantage of embodiments of the present invention that, by using a data-driven prediction of the artefact as is enabled by using the stimulus-response mapping to predict the artefact, where the stimulus-response mapping is determined based on a signal being identical to the received stimulus or a time-dependent signal derived therefrom and a signal corresponding to the measured response without requiring additional information or data, a more accurate prediction of the artefact can be made. It is an advantage of embodiments of the present invention that no prior knowledge or assumption about the shape of the artefact is required.

A further advantage of the data-driven approach of the present invention which uses the stimulus-response mapping for predicting the artefact is that, by basing the stimulus-response mapping calculation on signals corresponding to the stimulus and the response, the artefact prediction by the stimulus-response mapping includes a part that is correlated with the neural response. This means that the resulting corrected response has a reduction in the artefact which is correlated with the neural response. This helps to avoid the artefact being interpreted as part of the neural response in further processing of the neural response.

It is an advantage of embodiments of the present invention that, in contrast with e.g. template or function-based methods, stimulation artefacts can be compensated for in cases of continuous stimulations where artefacts from multiple pulses may overlap with each other.

According to a specific embodiment of the invention, the first signal corresponds to an electrical stimulus suitable for providing to an auditory nerve of the subject by a cochlear implant.

According to a specific embodiment of the invention, the stimulation artefact includes a contribution of electrical origin. For example, the artefact may be fully caused by an electrical signal, such as a signal from a cochlear implant. The artefact may include parts caused by an electrical signal, i.e. of electrical origin, and parts of non-electrical origin, for example vibration transmitted through the skull of a subject can cause electrodes to vibrate and thus cause an artefact in the measured response.

According to a particular embodiment of the invention, the step of identifying a feature of the determined stimulus-response mapping corresponding to the stimulation artefact may comprise a step of identifying a peak in the stimulus-response mapping.

According to a particular embodiment of the invention, the step of identifying a feature of the determined stimulus-response mapping corresponding to the stimulation artefact may comprise a step of identifying a feature having a latency smaller than a predetermined latency threshold.

According to a particular embodiment of the invention, the step of identifying a feature of the determined stimulus-response mapping corresponding to the stimulation artefact may comprise a step of identifying a feature having an amplitude greater than a predetermined amplitude threshold.

According to a particular embodiment of the invention, the method may further comprise, after performing step v), evaluating a correlation between the first signal and the for the stimulation artefact modified measured electrical response and, if the correlation is above a predetermined correlation threshold value, repeating steps ii) to v) with the stimulation artefact modified measured electrical response in place of the measured electrical response.

According to a particular embodiment of the invention, the method may comprise, if the correlation is below the predetermined correlation threshold value, outputting the stimulation artefact modified measured electrical response and/or the stimulus-response mapping determined in step ii).

According to a particular embodiment of the invention, the method may comprise, in instances in which steps i) to v) have been performed at least once: performing again at least steps i) and ii) and, after each instance of step ii) performed after the first instance of step ii), evaluating a mapping criterion and, if the mapping criterion is below a predetermined stop threshold value, outputting the stimulus-response mapping determined in step ii) and/or the stimulation artefact amplitude modified measured electrical response.

According to a particular embodiment of the invention, the method may comprise, if the mapping criterion is above the predetermined stop threshold value, continuing the method to step iii).

According to a particular embodiment of the invention, the method may further comprise, in step ii), iteratively applying a boosting algorithm or a hill climbing algorithm to determine a stimulus-response mapping.

According to a particular embodiment of the invention, within the boosting algorithm a cost may be applied to adding peaks in the measured electrical response at latencies less than a threshold latency value which is greater than a cost applied to adding peaks at latencies greater than the threshold latency value, wherein the threshold latency value is the time at which an expected biological response of the subject to the stimulus occurs.

According to a particular embodiment of the invention, within the boosting algorithm a peak in the EEG response at a latency of less than fifty (50) milliseconds (ms) may be restricted to an amplitude of less than a predetermined value.

According to a second aspect of the present invention there is provided a computer program comprising instructions which, when the program is executed by a computer, cause the computer to carry out the method of the first aspect.

According to a third aspect of the present invention there is provided a computer-readable medium comprising instructions which, when executed by a computer, cause the computer to carry out the method according to the first aspect.

For purposes of summarizing the invention and the advantages achieved over the prior art, certain objects and advantages of the invention have been described herein above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

The above and other aspects of the invention will be apparent from and elucidated with reference to the embodiment(s) described hereinafter.

BRIEF DESCRIPTION OF THE DRAWINGS

The invention will now be described further, by way of example, with reference to the accompanying drawings, wherein like reference numerals refer to like elements in the various figures.

FIG. 1c is a flowchart of a method according to embodiments of the present invention including a stopping criterion dependent on the result of a correlation between the stimulus and the response.

FIG. 2a is a plot of an EEG of a neural response.

FIG. 2b is a plot of the envelope of the stimulus presented during the recording of the EEG shown in FIG. 2a.

FIG. 3 is a plot of the stimulus-response mapping after one (solid line) and two (dashed line) iterations of a method according to embodiments of the present invention.

DETAILED DESCRIPTION OF ILLUSTRATIVE EMBODIMENTS

Figure 1A:
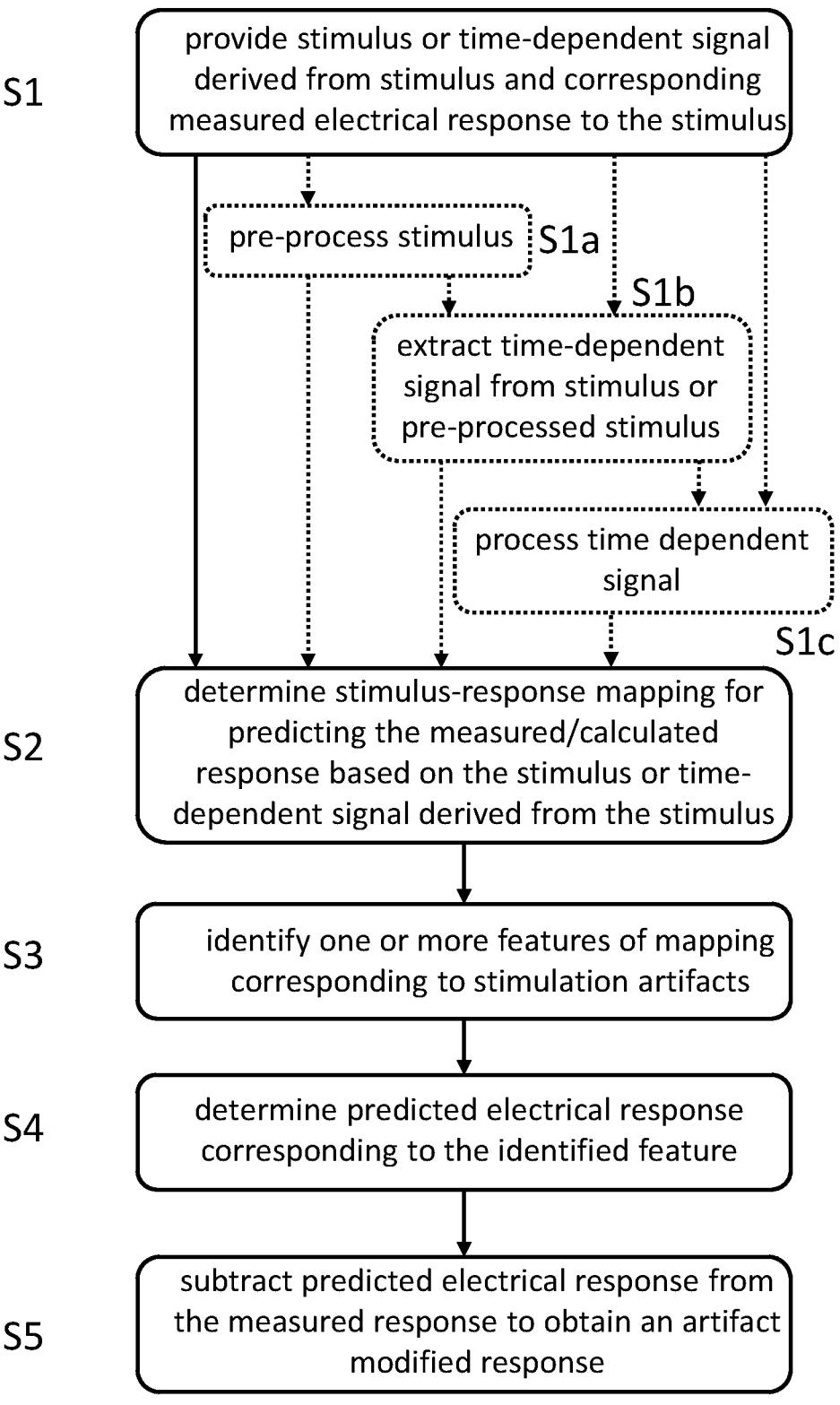
FIG. 1a is a flowchart of a method according to embodiments of the present invention.

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. Where an indefinite or definite article is used when referring to a singular noun e.g. "a" or "an", "the", this includes a plural of that noun unless something else is specifically stated. The term "comprising", used in the description and claims, should not be interpreted as being restricted to the means listed thereafter; it does not exclude other elements or steps. Thus, the scope of the expression "a device comprising means A and B" should not be limited to devices consisting only of components A and B. It means that with respect to the present invention, the only relevant components of the device are A and B. Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein. Moreover, the terms top, bottom, over, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein. In the drawings, like reference numerals indicate like features; and, a reference numeral appearing in more than one figure refers to the same element.

Referring to FIG. 1 a, a computer-implemented method of modifying a stimulation artefact in a measured electrical response of a subject, which may be a human or animal body, to a stimulus according to embodiments of the present invention comprises the following steps.

In Step S1, a first signal being a copy of a stimulus or a time-dependent signal derived from a stimulus, and a second signal being obtained as the corresponding measured electrical response to the stimulus are provided as input to the computer program.

The stimulus may be an electrical stimulus, for example an electrical signal suitable for outputting by a cochlear implant to an auditory nerve. The stimulus may be an auditory stimulus, for example an auditory signal suitable for outputting by a loudspeaker or headphones. The stimulus may be a mechanical stimulus, for example the output of bone conduction headphones or a bone-anchored hearing aid which function by causing the skull to vibrate and thus transmit sound to the inner ear. Another example of a mechanical stimulus is the output of a direct acoustic cochlear implant, being an implant which causes the cochlea to vibrate with a motor. In some embodiments, a signal identical to the stimulus in a raw format may be provided to the computer program and the method may further comprise a pre-processing step S1*a* comprising processing said signal used as stimulus in the raw format to extract data, for example to obtain one or more vectors of amplitudes and times. For example, in cochlear implant applications, the signal corresponding to the stimulus may be provided to the computer program as a sound file format for example mp3 or way, which is suitable for outputting in order to obtain an electrical response from the subject for example by playing through a loudspeaker; directly streaming from a computer to a sound processor of a cochlear implant through an audio cable; directly streaming from a computer to a sound processor of a cochlear implant using a direct interface without audio cable. The method may further comprise a stimulus pre-processing step comprising processing the sound file to extract data from the sound file, for example to obtain one or more vectors of audio amplitudes and corresponding times before inputting to the computer program implementing the method.

The measured electrical response of the subject to the stimulus may be any electrophysiological measurement, for example, without being limited hereto, an EEG.

In methods according to embodiments of the present invention a signal being the stimulus itself or a pre-processed version thereof as obtained in a pre-processing step or a time-dependent signal derived from the stimulus, is used in steps S2 onwards.

In some embodiments the method comprises an extraction step S1*b* between steps S1 and S2 for extracting a time-dependent signal from the stimulus provided in step S1 or from a pre-processed stimulus obtained in step S1*a*. The time-dependent signal is then used in steps S2 onwards. Alternatively, a time-dependent signal derived from the stimulus may be directly provided in step S1 and step S1*b* and, optionally, step S1*a*, may be omitted. In other embodiments, a signal equal to the stimulus itself or to a stimulus subjected to pre-processing as described hereinbefore, is used in steps S2 onwards.

In some embodiments a signal equal to the envelope of the stimulus or of the pre-processed stimulus is provided or obtained and is used in steps S2 onwards. For example, the time-dependent signal provided in step S1 may be the envelope of the stimulus. Alternatively, a signal equal to the stimulus itself may be provided in step S1 and the envelope of the signal may be obtained in step S1*b* directly from the signal equal to the stimulus or from a pre-processed form of that signal obtained in optional step S1*a*.

For example, in embodiments wherein the stimulus is, or is derived from, an audio signal that can be provided to a cochlear implant, preferably the envelope of the stimulus is extracted and used in the further steps; this is particularly advantageous as the envelope is one of the most important cues of speech required for good speech intelligibility. Speech intelligibility can be estimated from the envelope of the audio stimulus and the corresponding measured electrical response, for example EEG response, but this can be difficult to achieve if the measured electrical response comprises stimulation artefacts.

It has already been made clear that the computer program receives as input a first signal that is identical to the stimulus signal that was applied or that is a time-dependent signal derived from the applied stimulus and a second signal that is identical to the electrical signal that was measured in response (and possibly recorded or stored in some way). Therefore, the skilled person shall readily understand that where in the rest of this description is referred to the stimulus and the measured electrical response, reference is actually made to the copies of the stimulus signal and of the corresponding response used in the computer program.

When in the present application reference is made to "stimulation artefacts", reference may be made to an unintentional recorded stimulus signal or signals, for example waveforms, present in the measured electrical response to a stimulus. In other words, stimulation artefacts are artefacts directly or indirectly caused by the stimulus and are mostly problematic due to their correlation with the desired electrical (neural) response to or induced by the stimulus and/or due to their generally much larger amplitude than the desired electrical (neural) response in the measured electrical response which may impede the accuracy of the desired measured electrical (neural) response. Stimulation artefacts may be electrical, acoustical and/or mechanical in nature, without being limited thereto. For example, the stimulation artefacts may be caused by pickup by the EEG probes of electrical signals from the cochlear implant.

By using a method according to embodiments of the present invention, the measured electrical response, for example an EEG response, can be 'cleaned up' and made more suitable for speech intelligibility estimation. This is a consequence of the data-driven approach of the present invention, which uses the stimulus-response mapping for predicting the artefact: by basing the calculation of a stimulus-response mapping between the stimulus or a time-dependent signal derived from the stimulus on the one hand and the signal obtained as electrical response on the other hand, the stimulation artefact prediction by the determined or calculated stimulus-response mapping includes a part that is correlated with the neural response of the subject. This means that the resulting corrected measured electrical response has a modification, for example a reduction of the stimulation artefact, which is correlated with the neural response of the subject to the stimulus. This helps to minimize or even avoid the stimulation artefact being interpreted as part of the measured electrical (neural) response in further processing of the measured electrical (neural) response.

Optional step S1c provides for post-processing of the time-dependent signal, which is either received in step S1 or extracted in step S2. Post-processing can comprise filtering, resampling, re-referencing, normalisation, removal of non-electrical artefacts such as artefacts due to a muscle which is not of interest in the response, averaging across recording channels, averaging across repetitions, denoising, decomposition into components, component selection.

In some embodiments the time-dependent signal derived from the stimulus, whether provided in step S1 or obtained in step S1b, takes one or a combination of the following forms: a spectrogram of the stimulus or pre-processed stimulus; one or more frequency subbands of the stimulus or pre-processed stimulus; a fundamental waveform of the stimulus or pre-processed stimulus. If the stimulus is an audio signal that contains speech, the time-dependent signal may be a phoneme representation of the stimulus.

The second signal at the input of the computer program is a copy of the signal obtained as the measured electrical response to the stimulus. The measured electrical response of the subject, for example human or animal body, can be an electrophysiological response measured on one or more of the brain, a nerve, and a muscle. For example, the measured electrical response may be a response measured using electrodes placed on the brain (electrocorticography). The measured electrical response may be a response measured using electrodes placed on a muscle (electromyography). The measured electrical response may be a response measured using electrodes placed on the heart (electrocardiography). Electrodes may be surface electrodes attached to the skin, subcutaneous electrodes and/or implanted electrodes.

The stimulus may be an audio signal and the measured electrical response may be a neural response to the audio signal as measured using EEG electrodes on the scalp. Even if a cochlear implant is not present, the stimulus artefact may be present and caused by, for example, a transducer in an audio stimulus output device such as headphones or a loudspeaker. If a cochlear implant is present, the artefact may additionally or alternatively be caused by pickup by, for example, the probes of electrical impulses provided by the cochlear implant. The audio signal may be a pre-recorded audio signal which is played back using e.g. a loudspeaker. In some embodiments of the present invention, the cochlear implant may comprise an electrode for measuring an EEG response and the measured response may be a response measured using such an electrode. In some embodiments, environmental sounds, such as speech, can be picked up by a microphone of a sound processor or other device, translated into a sequence of electrical pulses, and provided to the cochlear implant. The stimulus can then be the recording of the audio signal or the electrical signal.

There may be other potential sources of a stimulation artefact. For example, an audio device for providing the stimulus which is located close to the subject's head can cause mechanical vibration of the electrodes, thus producing a mechanical artefact (which are also classified as stimulation artefacts) in the measured electrical response to the stimulus. Mechanical vibration of the electrode resulting in mechanical artefacts in the measured electrical response can be caused by use of bone conduction headphones or a bone-anchored hearing aid. Bone conduction headphones or a bone anchored hearing aid can also be the source of electrical signals causing electrical artefacts (which are also classified as stimulation artefacts). A mechanical stimulation such as a direct acoustic cochlear implant, an implant for causing the cochlea to vibrate with a motor, can cause stimulation artefacts in the measured electrical response by mechanical vibration of the electrodes (i.e. mechanical artefacts) and/or electrical signals which are picked up by the electrodes (i.e. electrical artefacts).

Put generally and as defined before, the stimulation artefact can be thought of as any unwanted and unintentional recorded or measured waveform(s), signal(s) or feature(s), caused by the stimulus either directly or indirectly, in the measured electrical response of the subject to the stimulus.

According to embodiments of the present invention, the stimulus may be a visual stimulus being an electrical (neural) signal for providing to a bionic ocular implant and which represents an image, and the measured electrical response may be a response measured using EEG or electrocortigraphy (ECoG) signals.

According to embodiments of the present invention, the stimulus may be an electrical stimulation for providing to the brain using a deep brain stimulator (DBS) implanted in the brain, such as those used to treat neurological conditions such as essential tremor, epilepsy, Parkinson's disease, or obsessive-compulsive disorder (OCD), and the corresponding measured electrical (neural) response may be a response measured using EEG or ECoG signals.

According to embodiments of the present invention, the method can be carried out using a single EEG channel's measured response, requiring only two electrodes. Multiple EEG channels are not needed, although in some embodiments more than one EEG channel may be used.

According to embodiments of the present invention, the method can be carried out using a single electrical EEG measurement. Although in some embodiments more than one electrical EEG measurement may be used.

According to embodiments of the present invention, the stimulus may be an electrical (neural) stimulation for providing to the brain using transcranial direct current or alternating current stimulation (tDCS or tACS respectively), where the stimulating electrodes for providing the stimulus are placed on the scalp, and the corresponding measured electrical response may be a response measured using EEG or ECoG signals.

According to embodiments of the present invention, the stimulus may be an electrical (neural) stimulation for providing to the heart muscles, for example as used in pacemakers, and the corresponding measured electrical response may be a response measured using electrocardiogram (ECG) signals.

According to embodiments of the present invention, the stimulus may be an electrical (neural) stimulation for application by a spinal cord implant to stimulate nerves in paralyzed limbs, and the corresponding measured electrical response may be a response measured using electromyography (EMG) signals.

According to embodiments of the present invention, the stimulus may be an electrical stimulation for providing to peripheral nerves, for example for treating chronic pain, either with an implanted or a transcutaneous stimulator. This may be referred to as peripheral nerve stimulation (PNS) and transcutaneous electrical nerve stimulation (TENS) respectively. The corresponding measured electrical response may be a response measured using EMG signals.

The method according to embodiments of the present invention may comprise a response pre-processing step between steps S1 and S2 comprising, for example, one or more of filtering, resampling, re-referencing, normalisation, removal or reduction of non-electrical artefacts such as stimulation artefacts due to a muscle which is not of interest in the response, averaging across recording channels, averaging across repetitions, denoising, decomposition into components, component selection.

In step S2, a stimulus-response mapping is determined, for example a temporal response function (TRF), for predicting the measured electrical response, wherein the determined mapping is based on the stimulus or the time-dependent signal derived from the stimulus. As will be described hereinafter in more detail, in some embodiments, steps S2 to S5 can be repeated and in such cases the for the stimulation artefact modified measured electrical response determined in the immediately preceding instance of step S5 is used in place of the measured electrical response in step S2. For clarity, in the following description, only the measured electrical response is referred to but it will be understood that this can also be the simulation artefact modified measured electrical response from the previous step S5.

The TRF is an example of a mapping between the stimulus input S(t) and the evoked electrical response r(t) it elicits. The measured electrical response is modelled as a linear combination of a weighting factor multiplied by the stimulus, where each instance of the time-dependent stimulus has a different latency. The TRF is then a vector of weighting factors, or amplitudes, for each corresponding latency value. The TRF therefore varies as a function of latency of the stimulus. This linear model can be formulated according to equation 1:

$$r_{pred}(t) = \Sigma_\tau TRF(\tau)S(t-\tau) + \epsilon(t) \tag{1}$$

where $r_{pred}(t)$ is the predicted neural response, $\epsilon(t)$ is a residual contribution to the evoked response not explained by the linear model, and $\tau$ is the latency variable.

The latency can be thought of as a shift in time between the predicted response and the stimulus. In general, the electrical (neural) response of the body to an electrical stimulus is not instantaneous and is delayed with respect to the stimulus. The delay can depend on many factors. For example, in cochlear implant applications the delay can depend on intelligibility of speech in an audio signal.

The stimulus-response mapping, e.g. the TRF, is preferably determined using an iterative method. The iterative method preferably uses a boosting or hill climbing algorithm.

In a boosting or hill climbing algorithm, the coefficients of the model to be estimated, e.g. the TRF or another mapping, are initially all set at zero. In each iteration, each coefficient is sequentially slightly varied. The improvement in model performance, for example the similarity of the predicted response to the measured response, is assessed for each variation in each coefficient. The changed coefficient that causes the largest improvement in the model performance is made permanent, and the remaining coefficients retain their values from the start of that iteration, i.e. only one coefficient is updated per iteration.

In the boosting algorithm, a first cost may be applied to adding peaks in the neural response at latencies less than a threshold latency value and a second cost may be applied to adding peaks at latencies greater than the threshold latency value, where the second cost is less than the first cost. The threshold latency value is the time after which no more stimulus artefact is expected or only an insubstantial contribution of stimulus artefact is expected. The threshold latency value is generally of the order of tens of milliseconds, depending on the particular application and the measurement apparatus used. The threshold latency value can be estimated, for example, by reviewing several measured neural responses and estimating the point after which the artefact has no significant amplitude. The threshold latency value can be estimated, for example, by a user who inspects the stimulus-response mapping and chooses an appropriate threshold latency. The threshold latency value can be estimated using a machine learning method trained on a set of TRFs and corresponding threshold latency values.

The iterations continue until a stopping criterion is fulfilled. This can be assessed, for example, by calculating a sum of squared differences between the response predicted by the mapping and the actual measured response and halting the boosting algorithm when this sum is less than a threshold value. However, other stopping criteria can be used. For example, the mean absolute error can be determined and compared with a predetermined threshold stopping value. The boosting algorithm can be halted once a predetermined maximum number of iterations have been carried out. The boosting algorithm can be halted once a stimulus-response mapping is achieved which contains a predetermined maximum number of maxima and/or minima. The first few maxima/minima produced in the mapping tend to be the most dominant or important maxima/minima, typically one corresponding to an artefact and a few corresponding to the largest neural responses. Due to noise in the signal, the algorithm can start adding more, often smaller, peaks after the first few are found. By restricting the number of peaks in the stimulus-response mapping, the addition of smaller peaks due to noise can be avoided.

In some embodiments, more than one coefficient can be updated per iteration. In such embodiments, preferably only a limited subset of coefficients may be updated per iteration, for example a subset of neighbouring coefficients.

The present invention is not limited to the use of a boosting or a hill climbing algorithm for estimating the stimulus-response mapping. For example, a regression method such as a linear regression method or a ridge regression method can be used. A deep learning method can be used.

The resulting mapping generally contains peaks at different latencies. Peaks at relatively small latencies, for example around zero (0) milliseconds (ms) to fifty (50) milliseconds (ms), tend to correspond to stimulation artefacts. Peaks at relatively longer latencies, for example greater than fifty (50) milliseconds (ms), tend to correspond to neural responses to the stimulus. In the presence of stimulation artefacts, at least the peak closest to zero (0) milliseconds (ms) can be assumed to be due to a stimulation artefact.

In step S3a feature of the determined mapping is identified wherein the feature corresponds to the stimulation artefact. This may be achieved, for example, by searching for one or more peaks in the determined mapping within a latency range which is close to zero latency values, for example within fifty (50) milliseconds (ms) on either side of zero latency. Other latency ranges around zero latency can be used, for example within forty (40) milliseconds (ms) or sixty (60) milliseconds (ms) on either side of zero latency, or an asymmetric range with respect to zero latency, for example from minus forty (−40) milliseconds (ms) to (plus) sixty (+60) milliseconds (ms), without being limited to these examples.

Taking again a TRF as example of a stimulus-response mapping, a peak in the determined TRF, also referred to as TRF peak, can be classified by its amplitude and its distance from zero latency, and a combination of these two parameters can be used to identify a peak corresponding to a stimulation artefact. TRF peaks due to one or more stimulation artefacts tend to be larger than peaks due to the expected or desired measured electrical (neural) response, but this may not necessarily always be the case. By classifying TRF peaks based on both their amplitude and their latency, it can be avoided that a large peak in the measured electrical (neural) response, having a latency outside the range within which the stimulation artefact may be present, is identified as being due to the stimulation artefact. A TRF peak can be a minimum or a maximum depending on the amplitude of the TRF elements. The polarity of an electrical (neural) TRF peak can be helpful for identification purposes.

For example, in auditory applications, a negative TRF peak around a latency of one hundred (100) milliseconds (ms) and a positive peak around a latency of two hundred (200) milliseconds (ms) may be expected. The polarity of TRF peaks can also change depending on location of the electrodes. Determining the TRF based on measurements taken from different electrodes can help in localizing the source of the electrical (neural) response.

A feature of the determined TRF corresponding to the stimulation artefact can be identified as a TRF peak having an amplitude which is greater than that of another feature of the determined TRF corresponding to an expected biological response of the subject to the stimulus, in other words having an amplitude greater than a predetermined amplitude threshold.

TRF peaks can be searched for in a latency range which has its limits at latencies at which a biological response of the subject to the stimulus is expected to occur. Corresponding latency thresholds can be predefined. Expected latency ranges for response peaks can be based on results previously reported in literature, where mean and variance in latency of common neural responses are described based on large sample sizes. For example, for auditory applications it is expected that the TRF includes a negative amplitude TRF peak at a latency around one hundred (100) milliseconds (ms) which can occur between around seventy (70) to around one hundred thirty (130) milliseconds (ms) post-stimulus, a positive amplitude TRF peak at a latency of around two hundred (200) milliseconds (ms) which can occur between around one hundred fifty (150) to around two hundred seventy-five (275) milliseconds (ms), and a positive amplitude TRF peak at a latency of around three hundred (300) millisecond (ms) which can occur between around two hundred fifty (250) milliseconds (ms) to three hundred fifty (350) milliseconds (ms).

In visual applications it is expected that the TRF includes a negative amplitude TRF peak between around one hundred fifty (150) milliseconds (ms) to two hundred (200) milliseconds (ms) post-stimulus.

After a TRF peak, either positive or negative in amplitude, is identified, the TRF coefficients corresponding to the TRF peak are identified along with the TRF coefficients at a latency less than the maximum latency of the TRF coefficients of the peak. The part of the TRF corresponding to stimulation artefacts is then isolated by setting all other TRF coefficients, except those corresponding to the stimulation artefacts, to zero.

In step S4a predicted electrical response corresponding to the identified TRF feature (of the determined mapping) is determined. Based on the identified TRF features (as explained before) an electrical response is predicted by applying equation 1, wherein the TRF function is replaced by a partial TRF defined or based on the identified TRF features. Hence, the partial TRF obtained in step S3 is used to predict an electrical (neural) response corresponding to the stimulation artefact(s), by using equation 1 with the partial TRF in place of the TRF.

In step S5 the predicted electrical response is subtracted from the measured electrical (neural) response of the subject to the stimulus, to obtain a for the stimulation artefact modified measured electrical response. This "for the stimulation artefact modified measured electrical response", also referred to as "the stimulation artefact modified measured electrical response", is defined as a modified measured electrical response, wherein the modified measured electrical response corresponds with the measured electrical response modified for the stimulation artefact or artefacts.

In embodiments of the present invention wherein steps S2 to S5 are performed more than once, the predicted electrical response is subtracted from the stimulation artefact modified measured electrical response obtained in the immediately preceding instance of step S5.

That is, a stimulation artefact modified measured electrical response is generated by subtracting the predicted electrical (neural) response corresponding to the stimulation artefact or artefacts from the actual measured electrical response.

Steps S2 to S5 can be repeated a predetermined number of times or can be repeated until a mapping criterion is satisfied and the mapping procedure is stopped. For example, referring to FIG. 1b, after each occurrence of step S2, from the second occurrence of step S2 onwards (i.e. steps S1 to S5 are performed and then at least steps S1 and S2 are performed again), a mean square sum of the stimulus-response mapping can be calculated in a specific range around zero latency (step S2a) and this can be compared to a predetermined stop threshold value (step S2b), below which it is considered that the stimulation artefact is sufficiently modified or removed. If the mean square sum is below the threshold value, the TRF can be provided as output, for example for estimating speech intelligibility in auditory applications (S2c). Additionally or alternatively, the stimulation artefact modified measured electrical response from the immediately preceding occurrence of step S5 can be provided as output.

Alternatively, referring to FIG. 1c, a correlation between the stimulus and the predicted electrical response can be calculated after each occurrence of step S5 (step S6a) and compared with a predetermined correlation threshold value (step S6b). The correlation can be, for example, a Spearman correlation, Pearson correlation, coherence, mutual information. If the correlation is below the threshold value or is not statistically significant, the mapping and/or the stimulation artefact modified measured electrical response can be provided as output (step S6c). If not, the method returns to step S2. During each iteration, the stimulus artefact is estimated and subtracted from the measured response (if the iteration is the first iteration), or from the stimulation artefact modified measured electrical response from the previous iteration.

Figure 1B:
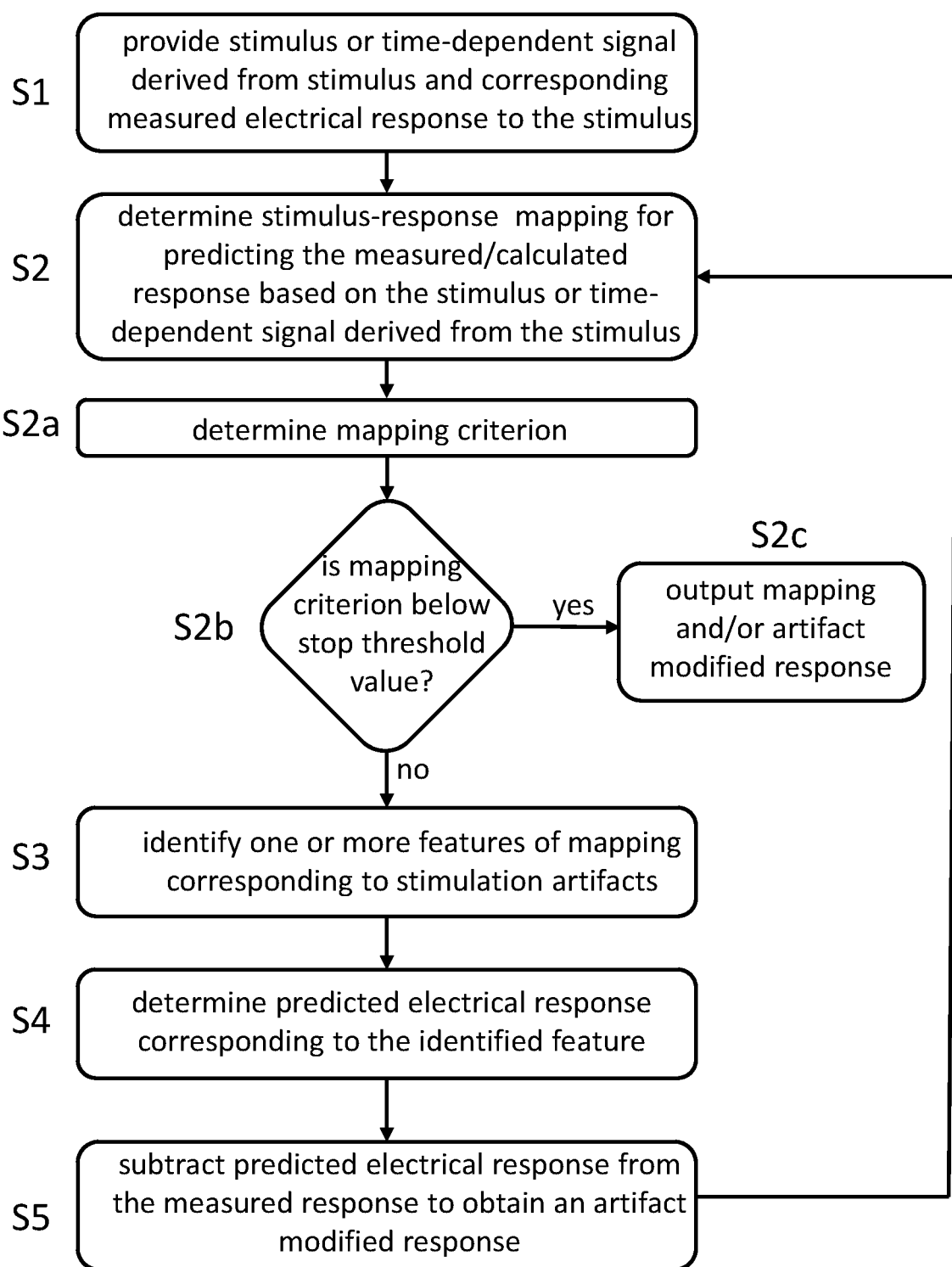
FIG. 1b is a flowchart of a method according to embodiments of the present invention including a stopping criterion dependent on the stimulus-response mapping.

In FIGS. 1b and 1c the optional steps S1a, S1b, S1c have been omitted for clarity but it will be understood that these optional steps can still be included in the methods shown in FIGS. 1b and 1c.

Referring to FIGS. 2 to 5, an example implementation of a method according to embodiments of the present invention is described.

The subject was a 47-year old woman with a cochlear implant in the right ear. The subject had 6 years of hearing experience with the implant. The original stimulus provided was 15 minutes of continuous speech, a story narrated by a female speaker in Flemish.

The neural response was measured using EEG in an electromagnetically shielded Faraday room using a BioSemi ActiveTwo 64-channel EEG recording system. The 64 electrodes were placed on the scalp in international 10-20 configuration with a head cap. Electrolyte gel was applied to ensure good electrode-skin impedances. The raw EEG was recorded at 16384 Hz and stored on a computer for later processing. The raw EEG was pre-processed by resampling to a lower sample rate of 128 Hz, re-referencing to vertex-referenced EEG montage Cz on top of the head, filtering between 0.5 Hz and 25 Hz, and normalizing.

The stimulus was processed as follows. First the envelope was extracted. Then the envelope was resampled to the same rate as the processed EEG i.e. 128 Hz. Finally the resampled envelope was filtered between 0.5 Hz and 25 Hz and normalized.

A five-second segment of the preprocessed EEG response is shown in FIG. 2a, and the stimulus envelope is shown in FIG. 2b.

Referring to FIG. 3, two mappings, in this particular case TRFs, are plotted as a function of latency, as estimated based on the envelope and measured response shown in FIGS. 2 (a) and 2 (b). The first TRF (solid line) has peaks $P_1$ around 0 milliseconds, which correspond to artefacts, and peaks $P_2$ at longer latencies, which correspond to neural responses. This is the TRF obtained after one performance of steps S1 to S5. The second TRF (dashed line) is the TRF obtained after repeating step S2 using the stimulation artefact modified measured electrical response calculated in the immediately preceding instance of step S5. It can be seen that the artefact peaks are no longer present. This artefact-modified TRF can then be used to predict artefact-reduced or artefact-free EEG or to derive objective measures for speech intelligibility.

Figures 4, 5:
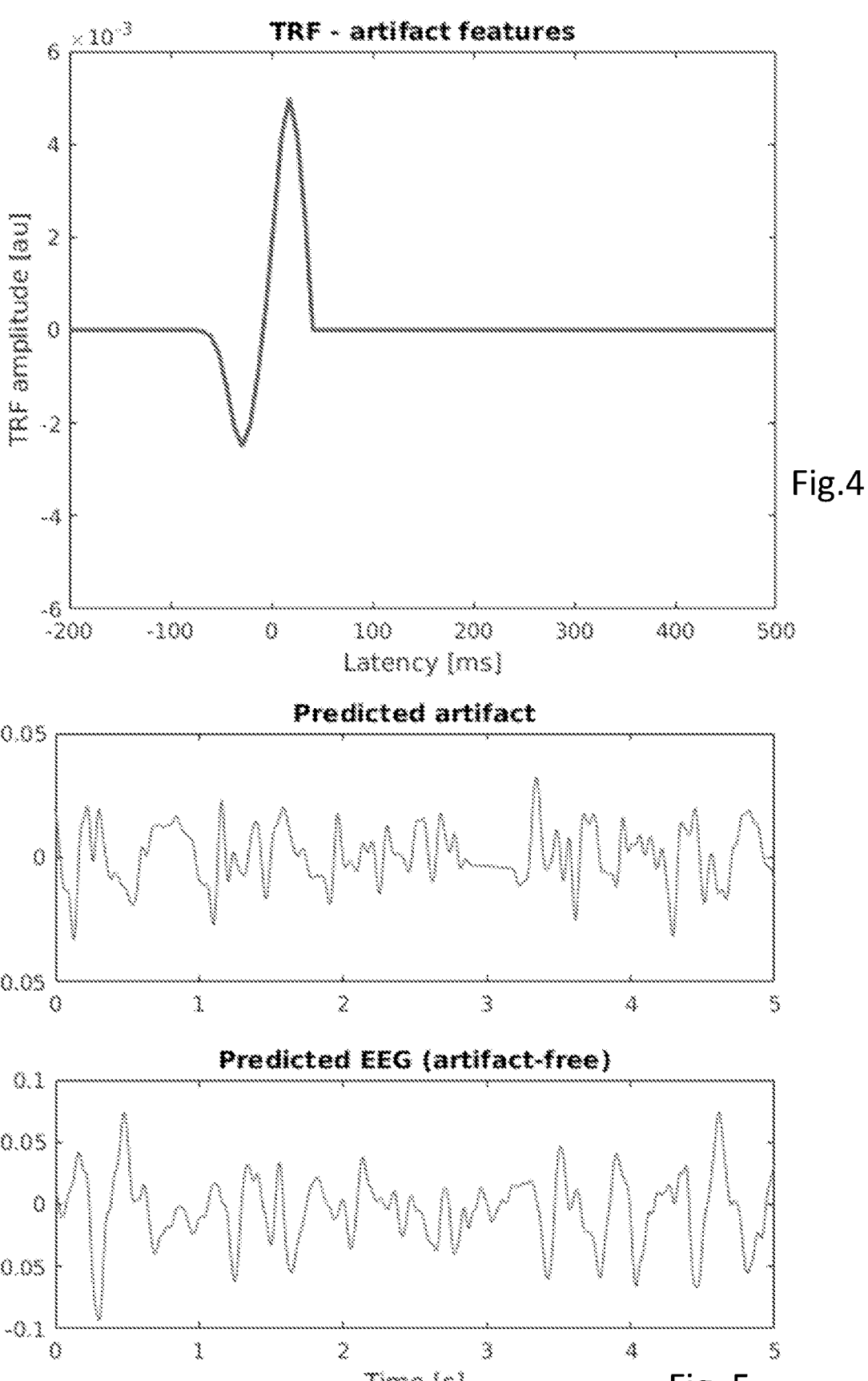
FIG. 4 is a plot of the stimulus-response mapping corresponding to the artefact features only.
FIG. 5 shows a plot of the predicted EEG response due to the artefact, and a plot of the artefact-amplitude modified EEG response obtained by subtracting the predicted EEG response due to the artefact from the measured EEG response.

FIG. 4 is a plot of a partial TRF corresponding to that part of the TRF identified as being due to the stimulus artefact in step S3 of the first iteration. FIG. 5 shows the stimulus artefact predicted by the artefact TRF of FIG. 4 (step S4), and the EEG signal obtained after subtraction of the stimulus artefact predicted response from the measured EEG response (step S5).

Figure 6A:
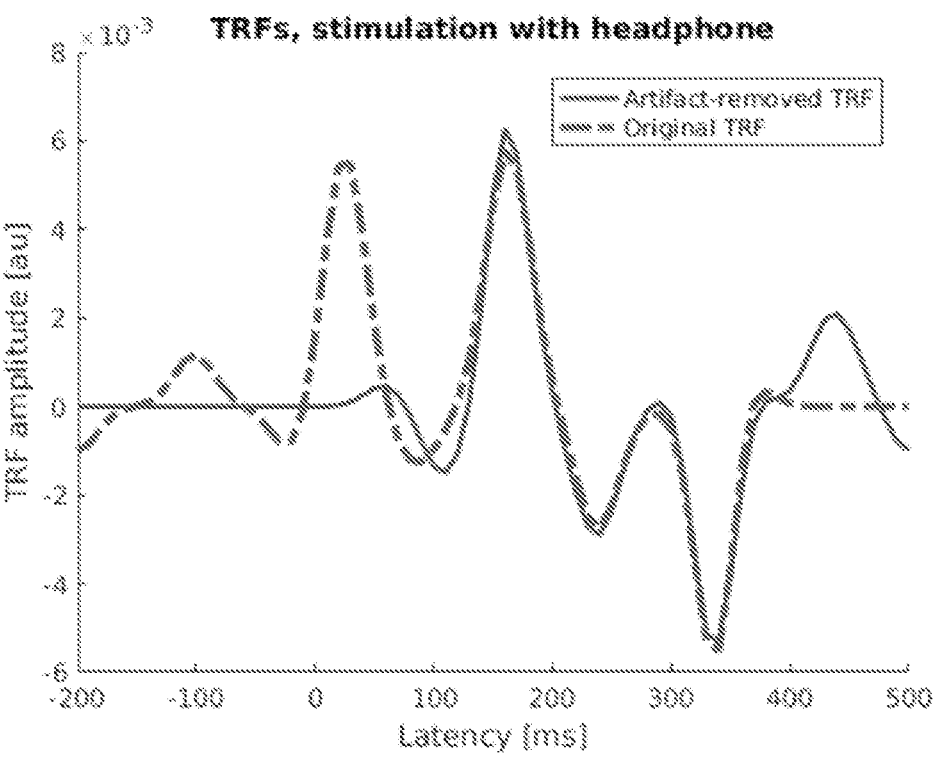
FIG. 6*a* is a plot of the TRF before any iterations of the method (dashed line) and after completing all iterations of the method (solid line) according to embodiments of the present invention.
Figure 6B:
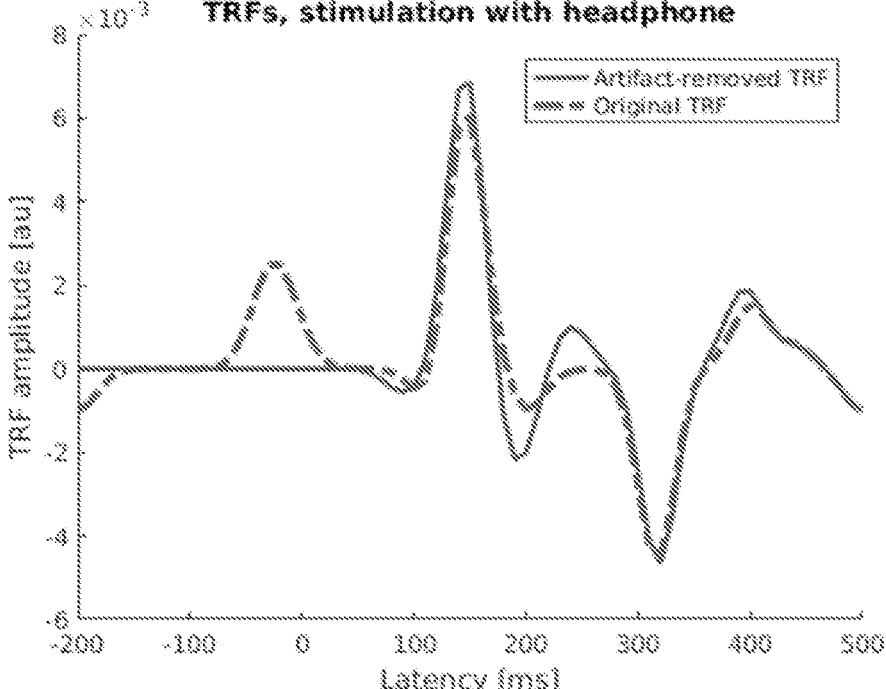
FIG. 6*b* is a plot of the TRF before any iterations of the method (dashed line) and after completing all iterations of the method (solid line) according to embodiments of the present invention.

Referring to FIGS. 6a, 6b, 7a and 7b, there is plotted four times two TRFs as function of latency, as estimated based on the envelopes and measured electrical responses (not shown) obtained from two different subjects. FIGS. 6a and 6b are related to subject one and showing TRFs calculated using EEG channels C1 and FC2, respectively.

Figure 7A:
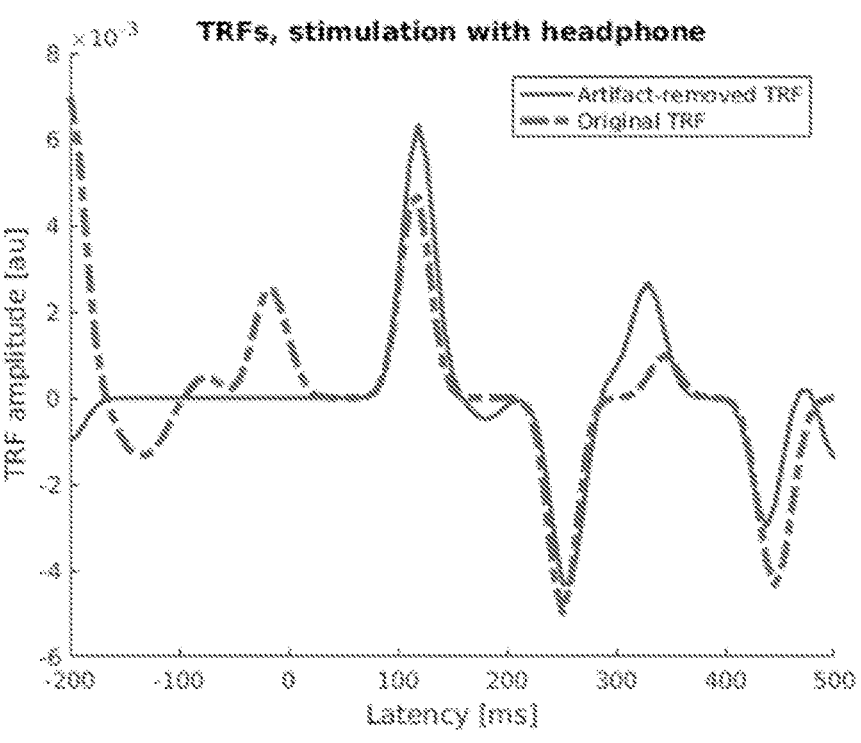
FIG. 7*a* is a plot of the TRF before any iterations of the method (dashed line) and after completing all iterations of the method (solid line) according to embodiments of the present invention.
Figure 7B:
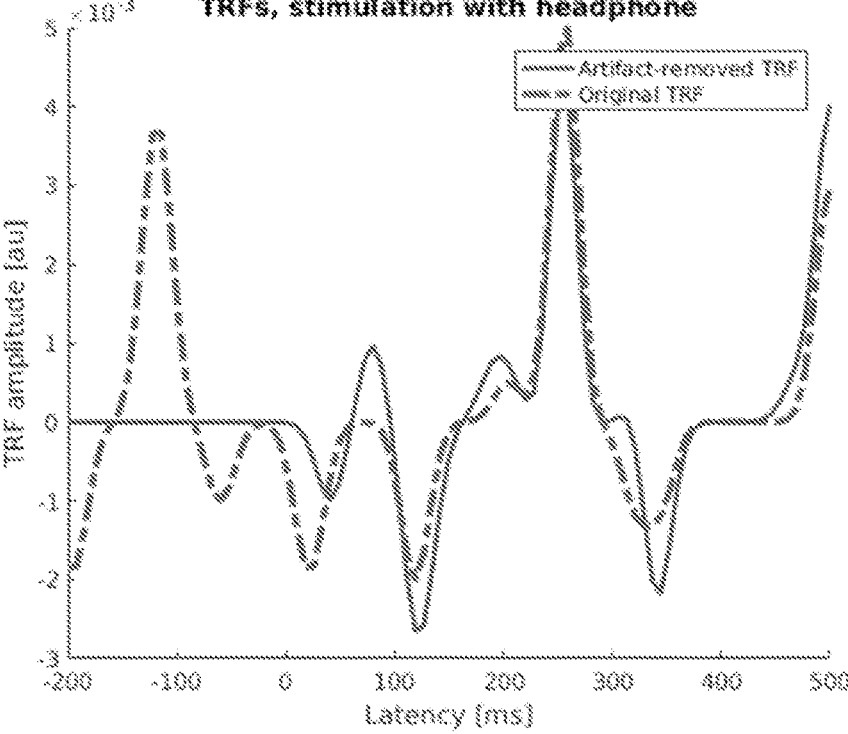
FIG. 7*b* is a plot of the TRF before any iterations of the method (dashed line) and after completing all iterations of the method (solid line) according to embodiments of the present invention.

FIGS. 7a and 7b are related to subject two and showing TRFs calculated using EEG channels FC2 and 1z, respectively. The subjects, who were normal-hearing, were wearing stimulus-emitting headphones and the electrical (neural) responses were measured using EEG under the same conditions as defined before.

The stimulus was processed as follows: first the envelope was extracted. Then the envelope was resampled to the same rate as the processed EEG i.e. 128 Hz. Finally the resampled envelope was filtered between 0.5 Hz and 25 Hz and normalized.

In each of FIGS. 6a to 7b, the first TRF (dashed lines) has TRF peaks around zero (0) milliseconds (ms), which corresponds to stimulation artefacts, and TRF peaks at longer latencies which corresponds to desired electrical (neural) responses. This first TRF is the TRF obtained after the initial TRF estimation using steps S1 and S2. The second TRF (solid line) is the output TRF obtained after multiple iterative applications of the stimulation artefact modifying steps S2-S5 until the TRF criterion is below its threshold value, as in FIG. 1b. It can be seen that the stimulation artefact peaks are no longer present. This artefact-modified TRF can then be used to predict artefact-reduced or artefact-free EEG or to derive objective measures for speech intelligibility.

While the invention has been illustrated and described in detail in the drawings and foregoing description, such illustration and description are to be considered illustrative or exemplary and not restrictive. The foregoing description details certain embodiments of the invention. It will be appreciated, however, that no matter how detailed the foregoing appears in text, the invention may be practiced in many ways. The invention is not limited to the disclosed embodiments.

Other variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A computer-implemented method of modifying a stimulation artefact in a measured electrical response of a subject to a stimulus, the method comprising:
  i) providing a first and a second signal, said first signal being a signal used as stimulus or a time-dependent signal derived from said stimulus and said second signal being a signal obtained as the measured electrical response to the stimulus;
  ii) determining a stimulus-response mapping between said first signal and said second signal;
  iii) identifying a feature of the determined stimulus-response mapping corresponding to said stimulation artefact;
  iv) determining a predicted electrical response corresponding to the identified feature of the determined stimulus-response mapping; and
  v) subtracting said predicted electrical response from said second signal to obtain a stimulation artefact modified measured electrical response.

2. The computer-implemented method according to claim 1, wherein the first signal corresponds to an electrical stimulus suitable for providing to an auditory nerve of the subject by a cochlear implant.

3. The computer-implemented method according to claim 1, wherein the stimulation artefact includes a contribution of electrical origin.

4. The computer-implemented method according to claim 1, wherein the step of identifying said feature of the determined stimulus-response mapping corresponding to the stimulation artefact comprises a step of identifying a peak in the stimulus-response mapping.

5. The computer-implemented method according to claim 1, wherein the step of identifying said feature of the determined stimulus-response mapping corresponding to the stimulation artefact comprises a step of identifying a feature having a latency which is smaller than a predetermined latency threshold.

6. The computer-implemented method according to claim 1, wherein the step of identifying said feature of the determined stimulus-response mapping corresponding to the stimulation artefact comprises a step of identifying a feature having an amplitude which is greater than a predetermined amplitude threshold.

7. The computer-implemented method according to claim 1, further comprising, after performing step v), evaluating a correlation between the first signal and the stimulation artefact modified measured electrical response and, if the correlation is above a predetermined correlation threshold value, repeating steps ii) to v) with the stimulation artefact modified measured electrical response in place of the measured electrical response.

8. The computer-implemented method according to claim 7, further comprising, if the correlation is below the predetermined correlation threshold value, outputting the stimulation artefact modified measured electrical response and/or the stimulus-response mapping determined in step ii).

9. The computer-implemented method according to claim 1 in which steps i) to v) have been performed at least once, further comprising performing again at least steps i) and ii) and, after each instance of step ii) performed after a first instance of step ii), evaluating a mapping criterion and, if the mapping criterion is below a predetermined stop threshold value, outputting the stimulus-response mapping determined in step ii) and/or the stimulation artefact modified measured electrical response.

10. The computer-implemented method according to claim 9, further comprising, if the mapping criterion is above the predetermined stop threshold value, continuing the method to step iii).

11. The computer-implemented method according to claim 1, wherein step ii) further comprises a step of iteratively applying a boosting algorithm or a hill climbing algorithm to determine a stimulus-response mapping.

12. The computer-implemented method according to claim 11, wherein within the boosting algorithm a cost is applied to adding peaks in the measured electrical response at latencies less than a threshold latency value which is greater than a cost applied to adding peaks at latencies greater than the threshold latency value,
  wherein the threshold latency value is a time at which an expected biological response of the subject to the stimulus occurs.

13. The computer-implemented method according to claim 11, wherein within the boosting algorithm a peak in the measured electrical response at a latency of less than fifty milliseconds is restricted to an amplitude of less than a predetermined value.

14. A computer-readable medium comprising instructions which, when executed by a computer, cause the computer to carry out the method of claim 1.

* * * * *